United States Patent [19]

Walker et al.

[11] 4,038,409

[45] July 26, 1977

[54] 1-PHENETHYLIMIDAZOLES

[75] Inventors: Keith A. M. Walker, Palo Alto; Michael Marx, Sunnyvale, both of Calif.

[73] Assignee: Syntex (U.S.A.) Inc., Palo Alto, Calif.

[21] Appl. No.: 662,786

[22] Filed: Mar. 1, 1976

[51] Int. Cl.$^2$ .................. A61K 31/415; C07D 233/60
[52] U.S. Cl. .............................. 424/273; 260/240 D; 260/240 J; 260/309
[58] Field of Search ................ 260/309, 240 D, 240 J; 424/273

[56] References Cited

U.S. PATENT DOCUMENTS

| | | | |
|---|---|---|---|
| 3,658,813 | 4/1972 | Godefroi et al. | 260/309 |
| 3,717,655 | 2/1973 | Godefroi et al. | 260/309 |
| 3,749,701 | 7/1973 | Engelhard et al. | 260/309 |
| 3,892,764 | 7/1975 | Metzger et al. | 260/309 |

*Primary Examiner*—Natalie Trousof
*Attorney, Agent, or Firm*—Tom M. Moran; William B. Walker

[57] ABSTRACT

Novel 1-phenethylimidazoles substituted at the position $\beta$ to the imidazole ring by an optionally substituted hydrocarbyl ester, thioester, or dithioester are useful as antimicrobial agents and as intermediates in the preparation of novel 1-phenethylimidazoles substituted at the position $\beta$ to the imidazole with a mercapto. Both the former and latter compounds are useful as intermediates in the preparation of certain 1-[$\beta$-(R-thio)phenethyl]-imidazoles.

33 Claims, No Drawings

1-PHENETHYLIMIDAZOLES

BACKGROUND OF THE INVENTION

1. Field of the Invention

This invention relates to novel 1-phenethylimidazoles substituted at the position β to the imidazole ring by a hydrocarbyl ester or a hydrocarbyl mono- or dithio-ester the use of these imidazoles as antimicrobial agents, the combination of these imidazoles with a suitable carrier, the preparation of these imidazoles, and the use of these imidazoles as intermediates in the preparation of 1-[β-(R-thio)phenethyl]-imidazoles.

2. Prior Art

It is generally known in the art that certain 1-(β-aryl)ethylimidazole ethers and amines have anti-fungal and anti-bacterial activity. See, for example, U.S. Pat. Nos. 3,717,655 and 3,839,574, both to Godefroi and Heeres and U.S. Pat. No. 3,658,813 to Godefroi and Schuermans. Representative of the ethers is the compound miconazole nitrate having the formula

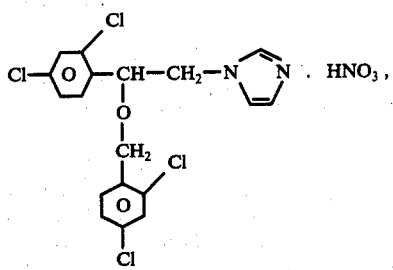

the active ingredient in Monistat[R] Cream sold by Ortho Pharmaceutical Co. Other 1-ethylimidazoles which are known include those disclosed in U.S. Pat. Nos. 3,796,704 and 3,892,764 to Metzger et al and U.S. Pat. No. 3,914,427 to Kramer et al. These, too, show antifungal activity.

An entirely new class of 1-[β-substituted phenethyl]-imidazoles has now been discovered which shows very good anti-fungal and anti-bacterial activity as well as anitprotozoal activity. These are the 1-phenethylimidazoles which are substituted at the position β to the imidazole with an ester or mono- or di-thioester moiety. The existence of related compounds such as (1,1-diphenyl-2-acetoxyethyl)imidazole or 1-(1-phenyl-1-t-butyl-2-acetoxyethyl)imidazole was disclosed in the broad disclosure U.S. Pat. No. 3,892,764, but, the compounds of the instant invention are chemically different and appear to be superior to the compounds of the 3,892,764 patent.

SUMMARY OF THE INVENTION

The first aspect of the present invention relates to novel imidazole derivatives and more particularly to 1-phenethylimidazoles having the formula:

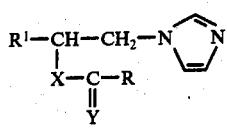

(I)

wherein

R is H, alkyl, phenylalkenyl, substituted phenylalkenyl, cycloalkyl, cycloalkyl lower alkyl, phenylalkyl, substituted phenylalkyl, phenyl and substituted phenyl, said substituted phenylalkenyl, substituted phenylalkyl and substituted phenyl containing at least one substituent on the phenyl moiety independently selected from the group consisting of halo, lower alkyl, lower alkoxy, and trifluoromethyl;

$R^1$ is phenyl optionally substituted with one or more substituents selected from the group consisting of halo, lower alkyl, and trifluoromethyl; and X and Y are independently sulfur or oxygen and the antimicrobial acid addition salts thereof.

The subject compounds of Formula (I), above, exhibit anti-fungal, anti-protozoal, and anti-bacterial activity against animal and human pathogens as well as anti-fungal activity against fungi of primarily agricultural importance. Thus, the subject compounds are found to be useful antimicrobials, having not only pharmaceutical but also agricultural and industrial applications. Thus, a further aspect of the present invention relates to methods of inhibiting the growth of fungi, protozoa, and bacteria by applying to a host object containing, or subject to attack by, fungi, protozoa or bacteria, a fungicidally, protozoicidally or bactericidally effective amount of a compound of this invention. A still further aspect of the present invention relates to compositions for pharmaceutical, agricultural, and industrial use, which compositions comprise the subject compounds of Formula (I) in combination with a suitable carrier.

Still another aspect of the present invention is the preparation of the compounds of Formula (I) set forth above. This will be discussed hereinafter more completely.

Finally, another aspect of this invention relates to the use of the compounds of this invention in preparing 1-[β-(R-thio)phenethyl]imidazoles.

Specific representative embodiments of the compounds, compositions, uses of and processes for preparing compounds of this invention will be discussed more completely and specifically hereinafter.

PREFERRED EMBODIMENTS

Compounds of the Invention

A. Definitions

The term "alkyl" as used in the specification and appended claims refers to a saturated, unbranched or branched acyclic hydrocarbon group containing 1 to 12 carbon atoms inclusive, such as methyl, ethyl, n-propyl, isopropyl, n-butyl, i-butyl, t-butyl, n-pentyl, n-heptyl, n-octyl, n-nonyl, n-dodecyl, and the like. The term "lower alkyl" refers to an alkyl group as previously defined containing 1 to 4 carbon atoms, inclusive, while lower alkoxy is a lower alkyl radical attached to an oxygen. The term "cycloalkyl" as used herein refers to a saturated, monocyclic hydrocarbon group having 5-8 ring carbon atoms. The term "cycloalkyl lower alkyl" refers to a cycloalkyl group as previously defined attached to an unbranched acyclic hydrocarbon group containing 1 to 3 carbon atoms, such as cyclopentylpropyl, cyclohexylmethyl, and cyclooctylethyl. The term "phenylalkenyl" refers to a hydrocarbon moiety in which the alkenyl portion containing 2 to 3 carbon atoms having carbon-carbon double bond unsaturation is attached to a phenyl ring, such as 3-phenyl-2-propenyl, styryl (i.e., 2-phenyl-1-ethenyl) and the like. The term "phenylalkyl" refers to a hydrocarbon moiety in which the alkyl portion contains 1 to 3 carbon atoms.

Representative examples include benzyl, 3-phenylpropyl and the like. The term "halo" as used herein refers to chloro, fluoro, and bromo. The term "anti-microbial acid addition salts" refers to salts of the subject compounds which possess the desired activity and which exhibit minimal undesirable biological or other effects. These salts are formed by reacting a compound of Formula (I) with inorganic acids such as hydrochloric acid, hydrobromic acid, sulfuric acid, nitric acid and phosphoric acid and the like, or organic acids such as acetic acid, propionic acid, glycolic acid, pyruvic acid, malic acid, malonic acid, succinic acid, maleic acid, fumaric acid, tartaric acid, citric acid, benzoic acid, cinnamic acid, mandelic acid, methanesulfonic acid, ethanesulfic acid, p-toluene sulfonic acid, and the like.

All compounds of Formula (I) have at least one chiral center, i.e., the carbon atom to which are attached the

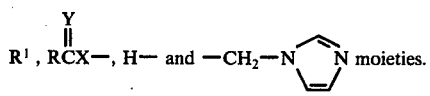

Accordingly, the compounds of the present invention may be prepared in either optically active form, or as a racemic mixture. Unless otherwise specified, the compounds described herein are all in the racemic form. However, the scope of the subject invention herein is not to be considered limited to the racemic form, but to encompass the individual optical isomers of the subject compounds.

If desired, racemic intermediates or final products prepared herein may be resolved into their optical antipodes by conventional resolution means known per se, for example, by the separation (e.g., fractional crystallization) of the diastereomeric salts formed by reaction of, e.g., racemic compounds of Formula (I) with an optically active acid, or the diastereomeric esters formed by reaction of the racemic alcohol precursors of compounds of Formula (II), infra or racemic mercapto precursors of Formula (IX), with an optically active acid. Exemplary of such optically active acids are the optically active forms of camphor-10-sulfonic acid, α-bromocamphor-π-sulfonic acid, camphoric acid, menthoxy-acetic acid, tartaric acid, malic acid, diacetyltartaric acid, pyrrolidone-5-carboxylic acid, and the like. The separated pure diastereomeric salts or esters may then be cleaved by standard means to afford the respective optical isomers of the compounds of Formula (I) or the precursor alcohols or mercaptans of Formulas (II) and (IX) respectively, infra. Particularly valuable is the resolution of an alcohol of Formula (II), e.g. by fractional crystallization of a salt with an optically active acid (e.g. dibenzoyl tartarate). The thus resolved alcohols or mercaptans may then be employed as discussed hereinafter to prepare the compounds of this invention.

In naming the compounds of this invention the following conventions will be followed (assuming e.g., that R¹ is 2,4-dichlorophenyl and R is ethyl):

1. When X and Y are both O, the compound is 1-[2,4-dichloro-β-(ethylcarbonyloxy)phenethyl]imidazole;

2. When X is S and Y is O, the compound is 1-2,4-dichloro-β-(ethylcarbonylthio)phenethyl]imidazole;

3. When X is O and Y is S, the compound is 1-[2,4-dichloro-β-(ethylthiocarbonyloxy)phenethyl]imidazole; and 4. When X and Y are both S, the compound is 1-[2,4-dichloro-β-(ethylthiocarbonylthio)phenethyl]imidazole.

In compounds where R is H, X and Y are both O, and R¹ is, for example 2,4-dichlorophenyl, the compound is named 1-[2,4-dichloro-β-(formyloxy)phenethyl]imidazole.

B. Specific Sub-Groups

Eminently suitable as the compounds of this invention are those wherein

R¹ is phenyl preferably substituted with from 1 to 3 halo substituents, particularly 4-halophenyl, 2,4-dihalophenyl (in which both halo are the same) or 2,4,6-trichlorophenyl, with one or two chloro substituents i.e., 4-chlorophenyl or 2,4-dichlorophenyl being most preferred.

Particularly suitable R substituents include alkyl of one to ten carbons such as methyl, ethyl, propyl, isopropyl, n-butyl, isobutyl, t-butyl, isoamyl, n-pentyl, n-hexyl, n-heptyl, n-octyl, n-nonyl, n-decyl and the like, straight chain alkyls being preferred, with straight chain alkyls of 3 to 9 carbons particularly preferred;

pheny preferably substituted with 1 to 3 (especially 1 or 2) halo substituents such as 4-halophenyl, 2,4-halophenyl and 3,4-halophenyl, with 4-chlorophenyl and 2,4-dichlorophenyl being the most particularly preferred;

benzyl preferably substituted on the phenyl ring with from 1 to 3 (preferably 1 or 2) halo substituents, such as 4-halo benzyl, 3,4-dihalobenzyl and 2,4-dihalobenzyl, with 4-chlorobenzyl and 2,4-dichlorobenzyl being the most particularly preferred; and styryl optionally substituted at the 4-position of the phenyl ring with a halo, preferably chloro.

Especially suitable as combinations of X and Y are those wherein X = S and Y = O or X and Y are both O.

An extremely preferred subclass of the compounds of this invention are those encompassed by the Formula of (I), above, wherein R¹ is 2,4-dichlorophenyl and R is straight chain alkyl of 3–9 carbons, phenyl preferably substituted with chloro at 1 or 2 positions (e.g. 4-chlorophenyl, 3,4-dichlorophenyl or 2,4-dichlorophenyl), benzyl being preferably ring substituted with 1 or 2 chloro substituents such as p-chlorobenzyl, 3,4-dichlorobenzyl or 2,4-dichlorobenzyl, styryl or p-chlorostyryl; and X and Y are each oxygen or X is sulfur while Y is O. Particularly preferred among those compounds having R as an alkyl and R¹ as 4-chlorophenyl or 2,4-dichlorophenyl are those wherein R is a straight chain alkyl of (i) 4–9 carbon atoms (especially 5–8) when X and Y are both O and (ii) 3–8 carbon atoms (especially 4–7) when X is S and Y is O.

Specific examples of each of these sub-groups may be found in the examples contained in the specification hereinafter.

UTILITY, FORMULATION AND ADMINISTRATION

The subject compounds of Formula (I) exhibit antifungal, anti-protozoal and anti-bacterial activity. For example, compounds of the present invention exhibit anti-fungal activity against human and animal pathogens such as

*Microsporum audouini, Trichophyton rubrum,*

*Microsporum gypseum, Trichophyton tonsurans,*
*Microsporum gypseum-canis, Candida albicans, and*
*Epidermophyton floccosum, Cryptococcus neoformans,*
*Trichophyton mentagrophytes.*

The compounds of the present invention also exhibit anti-fungal activity against fungi or primarily agricultural importance such as

*Aspergillus flavus, Aspergillus niger,*
*Cladosporium herbarum, Penicillium oxalicum,*
*Fusarium graminearum, Penicillium spinulosum, and*
*Penicllium notatum, Pithomyces chartarum.*

In addition, the compounds of the present invention exhibit anti-bacterial activity against human and animal pathogens, such as

*Staphylococcus aureus, Proteus vulgaris,*
*Streptococcus faecalis, Salmonella choleraesuis,*
*Corynebacterium acnes, Pasteruella multocida, and*
*Erysipelothrix insidiosa, Pseudomonas aeruginosa.*

*Escherichia coli,*

Furthermore, compounds represented by Formula (I) exhibit anti-protozoal activity against certain human pathogens such as *Trichomonas vaginalis.*

In view of the aforementioned activities, the subject compounds are found to be useful antimicrobials, having not only pharmaceutical but also agricultural and industrial application.

Accordingly, a further aspect of the present invention relates to compositions for pharmaceutical, agricultural, and industrial use, which compositions comprise the subject compounds of Formula (I) in combination with a suitable carrier. A still further aspect of the present invention relates to methods of inhibiting the growth of fungi, protozoa and bacteria by applying to a host object containing, or subject to attack by, fungi, protozoa or bacteria, a fungicidally, protozoicidally or bacteriocidally effective amount of a compound of the present invention or a suitable composition containing same.

In pharmaceutical application, compositions may be solid, semi-solid or liquid in form such as tablets, capsules, powders, suppositories, liquid solutions, suspensions, creams, lotions, gels, ointments and the like. Pharmaceutically accepable non-toxic carriers or excipients normally employed for solid formulations include tricalcium phosphate, calcium carbonate, kaolin, bentonite, talcum, gelatin, lactose, starch and the like; for semi-solid formulations there may be mentioned, for example, polyalkylene glycols, vaseline, petrolatum and other cream bases; for liquid formulations there may be mentioned, for example, water, oils of vegetable origin and low boiling solvents such as isopropanol, hydrogenated naphthalenes and the like. The pharmaceutical compositions containing the compounds of the present invention may be subjected to conventional pharmaceutical expedients such as sterilization and can contain conventional pharmaceutical excipients such as preservatives, stabilizing agents, emulsifying agents, salts for the adjustment of osmotic pressure and buffers. The compositions may also contain other therapeutically active materials.

The pharmaceutical compositions of this invention typically comprise a pharmaceutically acceptable, non-toxic carrier in combination with one or more compounds represented by Formula (I) in an amount effective for relief or prevention of the specific condition being treated. Since the active compounds of this invention exhibit anti-fungal, anti-bacterial and anti-protozoal activity over a wide range of concentration, the effective amount may vary. For example, in a topical formulation the amount of active ingredient may vary from about 0.1% by weight (%w) to about 10%w of the total pharmaceutical formulation, while other formulations may have from 5%w to 95%w or more active ingredient. Preferably the pharmaceutical compositions of this invention are formulated in unit dosage to form to facilitate administration (unit dosage being the amount of active ingredients administered on one occasion).

In pharmaceutical applications, the subject compounds and compositions may be administered to humans and animals by conventional methods, e.g. topically, orally, parenterally and the like. "Topical" administration includes intravaginal application while parenteral administration includes intramuscular as well as subcutaneous and intravenous injection. Intravenous injection of imidazole derivatives for certain systemic conditions has been demonstrated to be effective (see for example, Drugs, 9, 419–420 (1975), which describes the intravenous administration of Miconazole, i.e., 1-[2,4-dichloro-$\beta$-(2', 4'-dichlorobenzyloxy)phenethyl-]imidazole nitrate, to patients with systemic candidiasis). Topical application is the preferred method of administration in pharmaceutical applications. For such treatment, an area having an existing fungal, protozoal or bacterial growth, or to be protected against attack by fungi, protozoa, or bacteria, may be treated with the subject compounds or compositions by, for example, dusting, sprinkling, spraying, rinsing, brushing, dipping, smearing, coating, impregnating and the like.

The exact regimen for pharmaceutical administration of the compounds and compositions disclosed herein will necessarily be dependent upon the needs of the individual subject being treated, the type of treatment, e.g. whether preventative or curative, the type of organism involved and, of course, the judgment of the attending practitioner. In general, for systemic (e.g. oral or parenteral) administration it is expedient to administer the active ingredient in amounts of between about 1 and 100 mg/kg body weight per day (preferably between about 5 and 50 mg/kg body weight per day) preferably distributed over several applications (e.g. in 3 individual doses) in order to achieve effective results. For localized (e.g. topical) administration, however, proportionately less of the active ingredient is required.

In agricultural applications, the subject compounds may be applied directly to plants (e.g., seeds, foliage) or to soil. For example, compounds of the present invention may be applied to seeds alone or in admixture with a powdered solid carrier. Typical powdered carriers are the various mineral silicates, e.g., mica, talc, pyrophyllite, and clays. The subject compounds may also be applied to the seeds in admixture with a conventional surface-active wetting agent with or without additional solid carrier. Surface-active wetting agents that can be used are any of the conventional anionic, non-anionic or cationic types. As a soil treatment for fungi and the like, the subject comopounds can be applied as a dust in admixture with sand, soil or a powdered solid carrier such as mineral silicate with or without additional surface-active agent, or the subject compounds can be applied as an aqueous spray optionally containing a surface-active dispersing agent and a powdered solid carrier. As a foliage treatment, the subject compounds may be applied to growing plants as an aqueous spray which contains a surface-active dispersing agent with or without a powdered solid carrier and hydrocarbon solvents.

In industrial applications, the subject compounds may be used to control bacteria and fungi by contacting the pathogens with the compounds in any known matter. Materials capable of supporting bacteria and fungi may be protected by contacting, mixing or impregnating these materials with the subject compounds. In order to increase their effect, the subject compounds may be combined with other pesticidal control agents such as fungicides, bactericides, insecticides, miticides and the like. A particularly important industrial/agricultural use for the subject compounds of the present invention is as a food preservative against bacteria and fungi which cause deterioration and spoilage of foods.

PROCESS FOR PREPARING COMPOUNDS OF THE INVENTION

Compounds of this invention may be prepared from several unique processes. For example these compounds may be prepared from (A) an alcohol or a suitable metal salt thereof, e.g. a 1-(β-hydroxyphenethyl-)imidazole or its sodium salt, (B) a halide or reactive ester, e.g., a 1-(β-halophenethyl)imidazole, or (C) a mercaptan or a suitable metal salt thereof, e.g. a 1-(β-mercapto phenethyl)imidazole or its sodium salt.

A. When starting from an alcohol such as a 1-[substituted-β-hydroxyphenethyl]imidazole represented by Formula (II) the alcohol is reacted with a compound represented by $$\overset{Y}{\underset{\parallel}{RCA,}}$$

wherein A is a reactive leaving group, e.g. an acid chloride or an acid anhydride, to give the desired product according to the equation set forth below

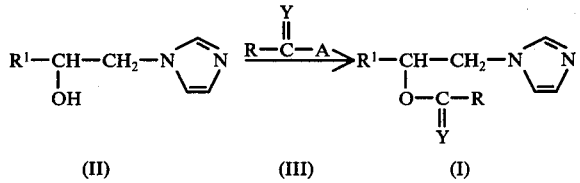

(II)   (III)   (I)

wherein A, R¹, R and Y have the values set forth hereinbefore. Thus, by reacting an appropriate acid chloride or anhydride with the appropriate 1-[β-hydroxyphenethyl]imidazole one obtains the corresponding 1-[β-(R-carbonyloxy)phenethyl]imidazole. Similarly from an R-thionacyl chloride one obtains a 1-[β-(R-thiocarbonyl-oxy)phenethyl]imidazole. When R is H, and Y is O, formic acid is used in place of the acid chloride or anhydride and the conditions are adjusted accordingly.

In carrying out the reaction of this process the 1-[β-hydroxyphenethyl]imidazole of Formula (II) is reacted directly with the acid chloride or anhydride preferably in the presence of a base while a suitable solvent is used for dissolving or suspending the reactants. Suitable solvents include dichloromethane, chloroform, pyridine, tetrahydrofuran, benzene, toluene, acetone, hexamethylphosphoramide, dimethylformamide and the like, while suitable bases include triethylamine, pyridine, potassium carbonate, sodium hydride, and the like. Generally the temperature is about −20° to 100° C. and the reaction is carried out at atmospheric pressure. At least 1 mole of the acid chloride or acid anhydride is reacted with one mole of the starting compound (II) for complete reaction to take place. Preferably the mole ratio is between about 1:1 and 2:1. When formic acid is used directly in place of the acid halide, no base is required.

The starting compounds of Formula (II) may be prepared by a variety of reaction sequences, the most important of which are discussed hereafter under "Preparation Of Starting Materials."

In some intances it may be preferable to first form a salt of the 1-[β-hydroxyphenethyl]imidazole before reaction with the acid chloride. For example, the sodium salt may be prepared by reacting the Formula (II) alcohol with sodium hydride and isolating if desired. Other suitable salts may be prepared by reacting the appropriate hydride, that is an alkali metal hydride or alkaline earth metal hydride with the 1-[β-hydroxyphenethyl]-imidazole. Examples of these bases include potassium hydride, lithium hydride, calcium hydride, and the like.

B. Another method for preparing the compounds of this invention comprises reacting an appropriate 1-[β-halo-phenethyl]imidazole with an alkali metal thiocarboxylate. This reaction sequence can be depicted by the following equation:

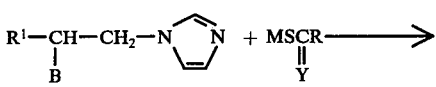

(V)   (IV)

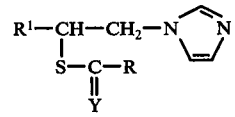

(I)

wherein M is a suitable metal such as sodium, potassium, or lithium; B is a reactive leaving group such as a tosylate, mesylate or halo, preferably chloro, and R, R¹, and Y have the definitions presented hereinbefore except that R is not H. Thus by reacting a 1-[β-halophenethyl]imidazole with, for example, the sodium salt of a thiocarboxylic acid (RCOSNa), the corresponding 1-β-(R-carbonylthio)phenethyl]imidazole is obtained, and in certain limited instances from the alkali metal salt of a dithiocarboxylic acid the corresponding 1-[β-R-thiocarbonylthio)phenethyl]imidazole is obtained. In this series of reactions generally the reactants are placed in a suitable solvent such as methanol, ethanol, acetone, tetrahydrofuran and are reacted at temperatures of from about 0° to 78° C, generally at atmospheric conditions. The reactants may be present at mole ratios of 1 to 3 moles of the salt of the thiocarboxylic acid per mole of the starting imidazole (V). When the acid-addition salt of a compound of Formula (V) is used, then at least 2 moles of the salt of the thiocarboxylic acid are preferably used. The starting imidazole depicted as Formula (V) of this process may be prepared by methods known in the art such as those disclosed in U.S. Pat. No. 3,679,697 to Kreider and Twelt. The salts of carboxylic acids are well known and may be prepared by methods known in the art while thiocarboxylic acids salts may be prepared by methods disclosed in E. E. Reid, *Organic Chemistry of Bivalent Sulfur*, Vol. IV, Chemical Publishing Co. Inc., New York, N. Y. (1962). As much of these disclosures as are pertinent are incorporated herein by reference.

A. Another process for making the compounds of Formula (I) wherein X is S involves reacting a mercaptide of the formula

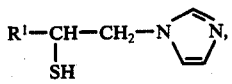
(VI)

wherein $R^1$ is previously defined, or an acid or base salt thereof with a suitable acid halide or anhydride represented by

where A is a reactive leaving group. Thus by reacting the mercaptide set forth in Formula (VI) above with an appropriate acid chloride

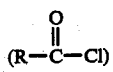

the corresponding 1-[β-(R-carbonylthio)phenethyl]imidazole is obtained. With more limited usefulness, by using certain thionacid chlorides

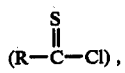

the corresponding 1-[β-(R-thiocarbonylthio)phenethyl]imidazole may be obtained. It appears that this procedure is of limited value where R is H. The compounds represented by Formula (VI) are prepared from certain compounds of this invention as represented by Formula (I), such as a 1[β-(R-carbonylthio)phenethyl]imidazole or acid addition salts thereof, e.g. 1-[2,4-dichloro-β-(methylcarbonylthio)phenethyl]imidazole. Such a compound is reacted with a suitable base such as sodium hydroxide under an inert gas such as nitrogen to give a compound of Formula (VI) or the acid or base salt thereof.

A mercaptide of Formula (VI) may also be prepared by similarly treating a compound of PA 789, filed even date herewith represented by the formula

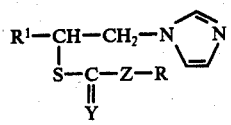
(VII)

wherein $R^1$ has the same definition as in this application, Y and Z are independently S or O, and R is alkyl, phenylalkenyl, substituted phenylalkenyl, cycloalkyl, cycloalkyl lower alkyl, phenylalkyl, substituted phenylalkyl, phenyl and substituted phenyl, said substituted phenyl, substituted phenylalkenyl, and substituted phenylalkyl containing at least one substituent on the phenyl moiety selected from the group consisting of halo, lower alkyl and trifluoromethyl. As much of PA 789 as is pertinent is incorporated herein by reference.

The acid chlorides useful as reactants in this process are well known in the art. Thionacid chlorides may be obtained by methods disclosed in the appropriate references in Reid, supra. The base salts of compounds of Formula (VI) may be prepared by reacting suitable compounds of Formula (I) or their acid addition salts, e.g. oxalate or nitrate, wherein X is sulfur with a suitable metal base such as an alkali metal hydroxide, e.g. sodium hydroxide or potassium hydroxide in a substantially inert solvent such as an oxygenated hydrocarbon, for example, methanol, at temperatures of about 0° to 50° C., preferably about 20° to 25° C. This salt may then be reacted with any suitable acid chloride or thionacid chloride as discussed above optionally in the presence of additional base (e.g. potassium carbonate) to form the compounds of this invention.

Alternatively the compounds represented by Formula (VI) or the base salts thereof may be prepared from a compound of PA 789 such as a 1-[β-(R-oxythiocarbonylthio)phenethyl]imidazole or its acid salt as exemplified by 1-[2,4-dichloro-β-(ethoxythiocarbonylthio)phenethyl]imidazole, by treating the compound with a suitable base such as sodium hydroxide preferably under an inert gas such as nitrogen at temperatures of about 0° C to 50° C, preferably about 20°-30° C. In either case the compounds of Formula (VI) may be prepared and reacted in situ in the presence of the appropriate acid chloride or they may be prepared first and isolated, then reacted with an acid chloride.

The amount of alkali metal hydroxide needed for the reaction will depend in part on whether the compound represented by Formula (VI) is a free base or the salt of a mono-basic acid (e.g. $HNO_3$) or a di-basic acid (e.g. oxalic acid). If the compound of Formula (I) is a free base at least 2 equivalents of the alkali metal hydroxide is required, while at least 3 equivalents, and preferably 3-4, are required if the compound (I) is the salt of a mono-basic acid and at least 4, preferably 4-5, equivalents of the alkali metal hydroxide if the compound (I) is the salt of a di-basic acid.

USE OF THE COMPOUNDS OF THIS INVENTION TO PREPARE OTHER COMPOUNDS

This process is based on the realization that certain compounds of the Formula (VI) may be reacted with a compound represented by the formula $R^2$-B, wherein B is halo or conventional leaving group and $R^2$ is defined below, to give certain compounds disclosed in U.S. Ser. No. 593,620, filed July 7, 1975 and PA 791 filed even date herewith, that is novel 1-[β-($R^2$-thio)phenethyl]imidazoles represented by the formula: filed July 7, 1975, that is Novel 1-[β-($R^2$-thio)phenethyl]-imidazoles represented by the formula:

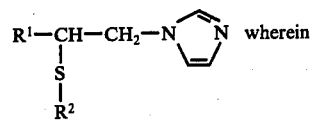
(VIII)

$R^1$ is previously defined and

R² is alkyl, alkenyl, aralkenyl, substituted aralkenyl, alkynyl, cycloalkyl, cycloalkyl alkyl, aralkyl, substituted aralkyl, or phenyl substituted with at least a nitro group at the 2- or 4- position, said substituted aralkenyl and substituted aralkyl containing at least one substituent on the aryl moiety selected from the group consisting of halo, lower alkyl, lower alkoxy, trifluoromethyl, nitro and cyano and said nitrophenyl optionally containing at least one other substituent selected from the group consisting of halo, lower alkyl, trifluoromethyl, nitro and cyano.

This process is based on the reaction between a compound of Formula (VI) or a suitable acid or base salt thereof and a suitable compound represented by R²B such as that set forth in the following reaction:

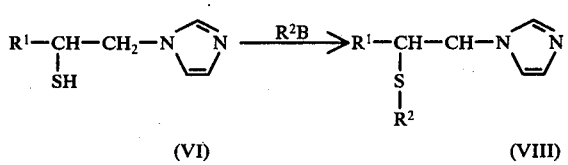

wherein R¹ and R are defined hereinbefore and B is a suitable leaving group such as mesylate, tosylate, or halo (Ha), e.g. bromo or preferably chloro. Thus, the process of this invention comprises preparing a compound of this invention according to any of the processes set forth hereinbefore, coverting the compound of this invention to a suitable compound represented by Formula (VI) and reacting said compound with a suitable compound represented by R²B to form the compound of Formula (VIII). The compounds of this invention are reacted with a suitable base such as an alkali metal hydroxide such as sodium hydroxide, potassium hydroxide, lithium hydroxide, and the like in a suitable solvent such as an oxygenated hydrocarbon such as methanol or ethanol in an inert atmosphere for a time sufficient to convert the compound of this invention to the base salt of a compound of Formula (VI). Generally, this will take up to about 2 hours at temperatures from 10° to about 50°, preferably at about 15° to 25° C. Once the base salt is obtained it is reacted with a suitable compound (R²B, preferably wherein B is chloro or bromo) to give the compounds of Formula (VIII). The second reaction between R²Ha and the base salt generally takes place in the presence of a suitable solvent at reaction temperatures of about 0° C to 80° C, normally about 25° C. Suitable solvents include methanol, ethanol, tetrahydrofuran, acetone and the like.

PREPARATION OF STARTING MATERIALS

The following preparations are given to show one of skill in the art how to prepare the starting reactants for one of the process aspects of this invention.

REACTION SCHEME A

In this reaction scheme the hydroxy compound of formula (II) is prepared by reduction of the corresponding ketone (IX) which in turn is prepared by reaction of an α-halo ketone (X) with imidazole;

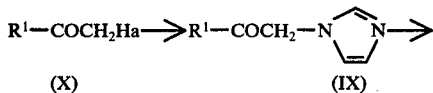

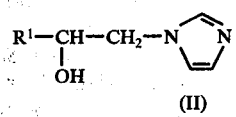

wherein Ha is chloro or bromo.

Certain α-halo ketones are available; others may be readily prepared by methods known in the art, for example, by halogenation of the corresponding methyl ketone, from the Friedel-Crafts reaction or from acid halides, or enol ethers.

The α-halo ketone is contacted with imidazole preferably in an inert organic solvent to afford the keto imidazole of Formula (IX). The reaction is carried out utilizing at least a molar amount and, preferably, an excess of imidazole relative to halo ketone. The reaction may be carried out in the absence of solvent or, preferably, in an inert organic solvent such as, for example, dimethylformamide, hexamethylphosphoramide, acetonitrile, and the like. The reaction is suitably carried out at a temperature initially between about −10° and 100° C, most preferably between about 0° and 25° C.

In the next step the keto imidazole of formula (IX) is reduced to the hydroxy imidazole of Formula (II) utilizing a conventional metal hydride reducing agent such as, for example, sodium borohydride. The reaction is suitably carried out in an alcoholic solvent such as, for example, methanol or ethanol at a reduced temperature, for example, between about −10° and +25° C, most preferably about 0° C.

Other methods for preparing the 1-[β-hydroxyphenethyl]imidazole (II) may be apparent to those skilled in the art, such as methods described in Godefroi et al, *J. Med. Chem.* 12, 784–791 (1966), and U.S. Pat. No. 3,717,655 to Godefroi and Heeres.

REACTION SCHEME B

In this preparation, the base salt of Formula (VIa) is prepared from a compound such as one represented by Formula (VII) according to the following reaction scheme.

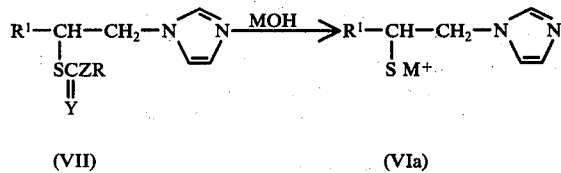

wherein R¹, R, Y, and Z are previously defined and M is a suitable metal. The compounds represented by Formula (VII) may be prepared as decribed in patent application PA- 789 filed even date herewith, and as much of that application as is pertinent is incorporated herein by reference. The compounds of Formula (VII) may be reacted as the free base as shown or as a suitable acid addition salt. For example, a suitable representative of Formula (VII) such as a 1-[substituted-β-(R-oxthiocarbonylthio)phenethyl]imidazole may be prepared by reacting an appropriate 1-phenethyl-imidazole with an alkali metal R xanthate in a suitable solvent. For example, 1-(β,2,4-trichlorophenethyl)imidazole hydrochloride may be reacted with potassium ethyl xanthate in ethanol to prepare 1-[2,4-dichloro-β-(ethoxythiocarbonylthio)phenethyl]imidazole. More complete details for the preparation of this compound and others of Formula (VII) are found in PA 789. A suitable acid addition salt such as the nitrate or oxalate may be prepared by reacting with nitric or oxalic acid and precipitating the salt. By adding the resulting salt under nitrogen to a solution of an alkali metal hydroxide (NaOH) in a suitable solvent (methanol) at room temperature, the alkali metal salt of the mercapto compound, represented by Formula (VIa) is obtained. The resulting solution may be reacted directly with a suitable acid chloride as discussed hereinbefore or the mercaptan may be isolated by acidifying the solution with ethereal hydrogen chloride, evaporating the solvent, basifying with dilute aqueous potassium carbonate and extracting the mixture with ether under an inert atmosphere. The extracts are washed, dried (MgSO$_4$) and the oxalate (or nitrate) salt precipitated.

EXAMPLES

The following specific examples are given to enable those skilled in the art to more clearly understand the practice of the present invention. These examples should not be considered as a limitation upon the scope of the invention but merely as being illustrative and representative thereof. In the examples that follow, experimental conditions such as reaction times, temperatures, etc. may be varied as is apparent to one of skill in the art. In enumerating compounds in the following examples, it is to be understood that the names represent the compound itself as well as the antimicrobial acid addition salts thereof, such as the nitrate or oxalate. Where appropriate for identification purposes, a representative salt is given with the corresponding melting point. In the case of an oxalate salt, there is one oxalate per imidazole, i.e., the salt is represented as

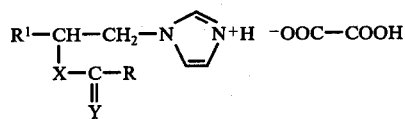

EXAMPLE 1

Preparation of
1-[β-(R-carbonyloxy)phenethyl]imidazoles

A. preparation of
1-[2,4-dichloro-β-(2,4-dichlorophenylcarbonyloxy)-phenethyl]imidazole

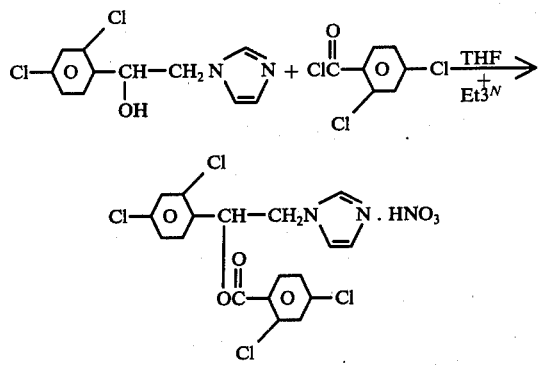

To a stirred ice cold solution of 0.64 g (2.5 × 10$^{-3}$ moles) of 1-[β-hydroxy-2,4-dichlorophenethyl]imidazole, 2 ml of triethylamine, and 30 ml of dry tetrahydrofuran, 0.65 g (3.12 × 10$^{-3}$ mole) of 2,4-dichlorobenzoyl chloride in 10 ml of dry tetrahydrofuran is added dropwise. After stirring the resulting mixture overnight at room temperature, the solvent is removed under reduced pressure and water is added. After extracting with ether, the combined ether portions are washed with water, dried (MgSO$_4$) and the nitrate salt precipitated by the dropwise addition of concentrated nitric acid (d = 1.42) until precipitation is complete.

Recrystallization from ethyl acetate/ethanol gave the nitrate salt of 1-[2,4-dichloro-β-[2,4-dichlorophenylcarbonyloxy)phenethyl]imidazole having a melting point of 163.5°–165° C (decomp.-foaming);

B. By following the procedure set forth in Part A of this example but employing a different acid chloride in place of 2,4-dichlorobenzoyl chloride, other compounds of this invention may be prepared, such as:

1-[2,4-dichloro-β-(n-butylcarbonyloxy)phenethyl-]imidazole;
1-[2,4-dichloro-β-(n-pentylcarbonyloxy)phenethyl-]imidazole;
1-[2,4-dichloro-β-(n-hexylcarbonyloxy)phenethyl-]imidazole, as nitrate mp 124°–126° C (decomp);
1-[2,4-dichloro-β-(n-heptylcarbonyloxy)phenethyl-]imidazole, as nitrate mp 99°–100.5° C
1-[2,4-dichloro-β-(n-octylcarbonyloxy)phenethyl-]imidazole;
1-[2,4-dichloro-β-(n-nonylcarbonyloxy)phenethyl-]imidazole;
1-[2,4-dichloro-β-(n-undecylcarbonyloxy)phenethyl-]imidazole, as nitrate mp 84.5°–86.5° C;
1-[2,4-dichloro-β-(3,4-dichlorophenylcarbonyloxy)-phenethyl]-imidazole;
1-[2,4-dichloro-β-(p-chlorophenylcarbonyloxy)phenethyl]-imidazole, as nitrate, mp 195°–196.5° C;
1-[2,4-dichloro-β-(p-chlorobenzylcarbonyloxy)phenethyl]-imidazole, as nitrate mp 154°–155.5° C (decomp);
1-[2,4-dichloro-β-(3,4-dichlorobenzylcarbonyloxy)-phenethyl]-imidazole;
1-[2,4-dichloro-β-(2,4-dichlorobenzylcarbonyloxy)-phenethyl]-imidazole;
1-[2,4-dichloro-β-(styrylcarbonyloxy)phenethyl-]imidazole;
1-[2,4-dichloro-β-(p-chlorostyrylcarbonyloxy)phenethyl]-imidazole;
1-(2,4-dichloro-β-(p-t-butylbenzylcarbonyloxy)-phenethyl-imidazole;
1-[2,4-dichloro-β-(p-t-butylphenylcarbonyloxy))phenethyl]-imidazole;
1-[2,4-dichloro-β-(p-bromophenylcarbonyloxy)phenethyl]imidazole;
1-[2,4-dichloro-β-(p-bromobenzylcarbonyloxy)phenethyl]imidazole;
1-[2,4-dichloro-β-(phenylcarbonyloxy)phenethyl-]imidazole;
1-[2,4-dichloro-β-(benzylcarbonyloxy)phenethyl-]imidazole;
1-[2,4-dichloro-β-(2-chlorophenylcarbonyloxy)phenethyl]imidazole; and
1-[2,4-dichloro-β-(formyloxy)phenethyl]imidazole
1-[2,4-dichloro-β-(3-phenylpropylcarbonyloxy)phenethyl]imidazole;
1-[2,4-dichloro-β-(3-p-chlorophenylpropylcarbonyloxy)phenethyl]-imidazole;
1-[2,4-dichloro-β-(2-cyclopentylethylcarbonyloxy)-phenethyl]imidazole;

1-[2,4-dichloro-β-(cyclohexylmethylcarbonyloxy)-phenethyl]imidazole;
1-[2,4-dichloro-β-(p-methoxyphenylcarbonyloxy)-phenethyl]imidazole;
1-[2,4-dichloro-β-(p-methoxybenzylcarbonyloxy)-phenethyl]imidazole; and
1-[2,4-dichloro-β-)p-t-butoxyphenylcarbonyloxy)-phenethyl]imidazole.

C. PREPARATION OF OTHER IMIDAZOLES HAVING DIFFERENT R¹ SUBSTITUENTS

Similarly, by substituting other 1-[β-hydroxyphenethyl]-imidazoles for 1-[2,4-dichloro-β-hydroxyphenethyl]imidazole and other acid chlorides for 2,4-dichlorobenzoyl chloride where appropriate in Part A of this example, other compounds of this invention may be prepared such as the following:

1-[β-(n-dodecylcarbonyloxy)phenethyl]imidazole;
1-[2,4-difluoro-β-(3,4-dichlorobenzylcarbonyloxy)-phenethyl]-imidazole;
1-[2,4-difluoro-β-(2,4-dichlorobenzylcarbonyloxy)-phenethyl]-imidazole; 1-[2,4-dibromo-β-(2,4-dichlorophenylcarbonyloxy)phenethyl]-imidazole;
1-[2,4-dibromo-β-(3,4-dichloroph enylcarbonyloxy)-phenethyl]-imidazole;
1-[2,4-dibromo-β-(3,4-dichlorobenzylcarbonyloxy)-phenethyl]-imidazole;
1-[2,4-dibromo-β-(2,4-dichlorobenzylcarbonyloxy)-phenethyl]-imidazole;
1-[2,4-dimethyl-β-(n-butylcarbonyloxy)phenethyl]imidazole;
1-[4-t-butyl-β-(n-butylcarbonyloxy)phenethy]-imidazole;
1-[4-t-butyl-β-(p-chlorobenzylcarbonyloxy)phenethyl]imidazole;
1-[4-t-butyl-β-(n-hexylcarbonyloxy)phenethyl]imidazole;
1-[3,4-dichloro-β-(p-chlorobenzylcarbonyloxy)phenethyl]-imidazole;
1-[3,4-dichloro-β-(p-chlorobenzylcarbonyloxy)phenethyl]imidazole;
1-[2,4,6-trichloro-β-(n-propylcarbonyloxy)phenethyl]imidazole;
1-[2,4,6-trichloro-β-(n-butylcarbonyloxy)phenethyl]imidazole;
1-[2,4,6-trichloro-β-(n-pentylcarbonyloxy)phenethyl]imidazole;
1-[2,4,6-trichloro-β-(n-hexylcarbonyloxy)phenethyl]imidazole;
1-[2,4,6-trichloro-β-(p-fluorobenzylcarbonyloxy)-phenethyl]-imidazole;
1-[2,4,6-trichloro-β-(p-chlorobenzylcarbonyloxy)-phenethyl]-imidazole;
1-[2,4,6-trichloro-β-(p-chlorophenylcarbonyloxy)-phenethyl]-imidazole;
1-[2,4-dibromo-β-(n-butylcarbonyloxy)phenethyl]imidazole;
1-[2,4-dibromo-β-(n-pentylcarbonyloxy)phenethyl]imidazole;
1-[2,4-dibromo-β-(n-hexylcarbonyloxy)phenethyl]imidazole;
1-[2,4-dibromo-β-(n-heptylcarbonyloxy)phenethyl]imidazole;
1-[2,4-dimethyl-β-(n-heptylcarbonyloxy)phenethyl]imidazole;
1-[β-(3-cyclohexylpropylcarbonyloxy)phenethyl]imidazole;
1-[2,4-dimethyl-β-(n-octylcarbonyloxy)phenethyl]imidazole;
1-[2,4-dimethyl-β-(3,4-dichlorobenzylcarbonyloxy)-phenethyl]-imidazole;
1-[2,4-dimethyl-β-(2,4-dichlorobenzylcarbonyloxy)-phenethyl]-imidazole;
1-[4-chloro-β-(n-butylcarbonyloxy)phenethyl]imidazole;
1-[4-chloro-β-(n-pentylcarbonyloxy)phenethyl]imidazole;
1-[4-chloro-β-(n-hexylcarbonyloxy)phenethyl]imidazole;
1-[4-chloro-β-(n-heptylcarbonyloxy)phenethyl]imidazole;
1-[4-chloro-β-(n-octylcarbonyloxy)phenethyl]imidazole;
1-[4-chloro-β-(n-nonylcarbonyloxy)phenethyl]imidazole;
1-[4-chloro-β-(3,4-dichlorophenylcarbonyloxy)phenethyl]-imidazole;
1-[4-chloro-β-(2-chlorophenylcarbonyloxy)phenethyl]imidazole, as oxalate mp 201°–203° C (decomp.-foaming);
1-[4-chloro-β-(p-chlorophenylcarbonyloxy)phenethyl]imidazole; as nitrate mp 193°–195.5° C (decomp-foaming);
1-[4-chloro-β-(p-chlorobenzylcarbonyloxy)phenethyl]imidazole; as oxalate m.p. 158°–159.5° C (decomp-foaming);
1-[4-chloro-β-(2,4-dichlorobenzylcarbonyloxy)-phenethyl-]-imidazole;
1-[4-chloro-β-(2,4-dichlorophenylcarbonyloxy)phenethyl]imidazole; and
1-[4-chloro-β-(2,4-dichlorobenzylcarbonyloxy)phenethyl]imidazole;
1-[4-chloro-β-(styrylcarbonyloxy)phenethyl]imidazole; and
1-[4-chloro-β-(p-chlorostyrylcarbonyloxy)phenethyl]imidazole.

EXAMPLE 2

Preparation of 1-(β-[R-carbonylthio]phenethyl)imidazoles

A. Preparation of OF 1-[2,4-dichloro-β-(n-pentylcarbonyl-thio)phenethyl]imidazole To a solution of 0.16g (4.0×10⁻³ mole) of sodium hydroxide in a 40 ml of anhydrous methanol 0.42g (1×10⁻³ mole) of 1-[β-(ethoxythiocarbonylthio-2,4-dichlorophenethyl]imidazole nitrate was added under nitrogen. After completion of hydrolysis (circa 30 minutes), 500 mg. of anhydrous potassium carbonate and 0.54g (4.0×10⁻³ mole) of n-hexanoyl chloride were added and the mixture stirred under nitrogen for thirty minutes at room temperature. After removal of the solvent under reduced pressure, water was added and the product extracted with ether.

The extracts were washed with water, dried (MgSO₄) and treated with nitric acid (d=1.42) until precipitation of the nitrate salt (0.42 g) is complete. Recrystallization from ethyl acetate gave 1-[2,4-dichloro-β-(n-pentylcarbonylthio)-phenethyl]imidazole, nitrate, mp 122°–123.5° C (decomp).

B. By following the procedure set forth in Part A of this example but substituting the appropriate hydrocarbon acid chloride for n-hexanoyl chloride, other (1-[2,4- dichloro-β-(R-carbonylthio)phenethyl]imidazoles are prepared. These include the following:

1-[2,4-dichloro-β-(n-propylcarbonylthio)phenethyl-]imidazole;
1-[2,4-dichloro-β-(n-butylcarbonylthio)phenethyl-]imidazole;
1-[2,4-dichloro-β-(n-hexylcarbonylthio)phenethyl-]imidazole;
1-[2,4-dichloro-β-(n-heptylcarbonylthio)phenethyl-]imidazole; as oxalate, mp 133.5°-134.5° C (decomp);
1-[2,4-dichloro-β-(n-octylcarbonylthio)phenethyl-]imidazole;
1-[2,4-dichloro-β-(2,4-dichlorophenylcarbonylthio)-phenethyl]-imidazole;
1-[2,4-dichloro-β-(3,4-dichlorophenylcarbonylthio)-phenethyl]-imidazole;
1-[2,4-dichloro-β-(p-chlorophenylcarbonylthio)phenethyl]-imidazole, as nitrate, mp 149°-150.5° (decomp);
1-[2,4-dichloro-β-(p-chlorobenzylcarbonylthio)phenethyl]-imidazole, as nitrate, mp 136.5°-139° C (decomp-foaming);
1-[2,4-dichloro-β-(2,4-dichlorobenzylcarbonylthio)-phenethyl]-imidazole;
1-[2,4-dichloro-β-(3,4-dichlorobenzylcarbonylthio)-phenethyl]-imidazole;
1-[2,4-dichloro-β-(p-methylphenylcarbonylthio)phenethyl]imidazole;
1-[2,4-dichloro-β-(styrylcarbonylthio)phenethyl-]imidazole; as nitrate, mp 139°-141° C (decomp.-foaming);
1-[2,4-dichloro-β-(p-methylcarbonylthio)phenethyl]-imidazole;
1-[2,4-dichloro-β-(p-bromophenylcarbonylthio)phenethyl]imidazole;
1-[2,4-dichloro-β-(p-bromobenzylcarbonylthio) phenethyl imidazole;
1-[2,4-dichloro-β-(o-chlorophenylcarbonylthio)phenethyl]-imidazole; as nitrate, mp 159°-161° C (decomp);
1-[2,4-dichloro-β-(m-chlorophenylcarbonylthio)phenethyl]imidazole;
1-[2,4-dichloro-β-(p-fluorobenzylcarbonylthio)phenethyl]imidazole;
1-[2,4-dichloro-β-(cyclohexylcarbonylthio)phenethyl-]imidazole;
1-[2,4-dichloro-β-(cyclooctylcarbonylthio)phenethyl-]imidazole;
1-[2,4-dichloro-β-(phenylcarbonylthio)phenethyl-]imidazole; and
1-[2,4-dichloro-β-(benzylcarbonylthio)phenethyl-]imidazole as nitrate, mp 115°-116° C (decomp-foaming).

C. Other imidazoles of Formula (I) having different $R^1$ substituents may be similarly prepared by substituting other 1-[β-(sodiumthic)phenethyl]imidazoles for 1-[2,4-dichloro-β-(sodiumthic) phenethyl]imidazole formed in part A of this example and the appropriate acid chloride for the n-hexanoyl chloride.

Other imidazoles of this invention include compounds such as the following:

1-[2,4-dibromo-β-(p-chlorobenzylcarbonylthio)phenethyl]imidazole;
1-[2,4-dibromo-β-(p-chlorophenylcarbonylthio)phenethyl]imidazole;
1-[2,4-dibromo-β-(n-pentylcarbonylthio)phenethyl-]imidazole
1-[2,4-dibromo-β-(n-hexylcarbonylthio)phenethyl-]imidazole;
1-[2,4-dibromo-β-(n-heptylcarbonylthio)phenethyl-]imidazole;
1-[2,4-difluoro-β-(n-octylcarbonylthio)phenethyl-]imidazole;
1-[2,4,6-trichloro-β-(methylcarbonylthio)phenethyl]-imidazole;
1-[2,4,6-trichloro-β-(ethylcarbonylthio)phenethyl-]imidazole;
1-[2,4,6-trichloro-β-(n-propylcarbonylthio)phenethyl-]imidazole;
1-[2,4,6-trichloro-β-(n-butylcarbonylthio)phenethyl-]imidazole;
1-[2,4,6-trichloro-β-(p-fluorophenylcarbonylthio)-phenethyl]-imidazole;
1-[2,4,6-trichloro-β-(o-fluorophenylcarbonylthio)-phenethyl]-imidazole;
1-[2,4,6-trichloro-β-(p-fluorobenzylcarbonylthio)-phenethyl]-imidazole;
1-[2,4,6-trichloro-β-(p-chlorobenzylcarbonylthio)-phenethyl]-imidazole;
1-[2,4,6-trichloro-β-(p-chlorophenylcarbonylthio)-phenethyl]-imidazole;
1-[2,4,6-trimethyl-β-(n-hexylcarbonylthio)phenethyl-]imidazole;
1-[2,4,6-trimethyl-β-(p-chlorophenylcarbonylthio)-phenethyl]-imidazole;
1-[2,4,6-trimethyl-β-(p-chlorobenzylcarbonylthio)-phenethyl]-imidazole;
1-[4-t-butyl-β-(phenylcarbonylthio)phenethyl-]imidazole;
1-[β-(t-butylbenzylcarbonylthio) phenethyl]imidazole;
1-[4-chloro-β-(n-propylcarbonylthio)phenethyl-]imidazole;
1-[4-chloro-β-(n-butylcarbonylthio)phenethyl-]imidazole;
1-[4-chloro-β-(n-pentylcarbonylthio)phenethyl-]imidazole;
1-[4-chloro-β-(n-hexylcarbonylthio)phenethyl-]imidazole;
1-[4-chloro-β-(n-heptylcarbonylthio)phenethyl-]imidazole;
1-[4-chloro-β-(n-octylcarbonylthio)phenethyl-]imidazole;
1-[4-chloro-β-(2,4-dichlorophenylcarbonylthio)phenethyl]-imidazole;
1-[4-chloro-β-(3,4-dichlorophenylcarbonylthio)phenethyl]-imidazole;
1-[4-chloro-β-(p-chlorophenylcarbonylthio)phenethyl-]imidazole;
1-[4-chloro-β-(p-chlorobenzylcarbonylthio)phenethyl-]imidazole;
1-[4-chloro-β-(2,4-dichlorobenzylcarbonylthio)phenethyl]imidazole;
1-[4-chloro-β-(3,4-dichlorobenzylcarbonylthio)phenethyl]imidazole;
1-[4-chloro-β-(styrylcarbonylthio)phenethyl]imidazole;
1-[2,4-dibromo-β-(p-chlorobenzylcarbonylthio)phenethyl]imidazole; and
1-[2,4-dibromo-β-(p-chlorophenylcarbonylthio)phenethyl]imidazole.

EXAMPLE 3

Preparation of 1-[βR-thiocarbonyloxy)phenethyl]imidazoles

A. The sodium salt of 1-[2,4-dichloro-β-hydroxyphenethyl]-imidazole is prepared by adding 240 mg of a dispersion of 56% w sodium hydride in mineral oil to 1.30 g of 1-[2,4-dichloro-β-hydroxyphenethyl]imidazole in 5 ml. hexamethylphosphoramide under nitrogen and the mixture stirred at 10°–25° C for 1 hour and at 50° for a further hour to form a solution of the desired sodium salt. The solution is then cooled to ca. 5° C and treated with 870 mg. of thiobenzoyl chloride in 1 ml. of hexamethylphosphoramide. The solution is stirred for one hour at room temperature, 6 hours at 50° C and poured into water. The product is extracted with ether and the extracts washed with three, 30 ml portions of water and dried over magnesium sulphate. The solution is then concentrated and nitric acid (d = 1.42) is added dropwise until precipitation is complete. Recrystallization from ethyl acetate gave the nitrate salt of 1-[2,4-dichloro-β-(phenethiocarbonyloxy)phenethyl]imidazole.

B. By following the procedure of part A of this example but employing other appropriate (substituted) hydrocarbon thiocarbonyl chlorides the following products may be prepared:

1-[2,4-dichloro-β-(n-propylthiocarbonyloxy)phenethyl]imidazole;
1-[2,4-dichloro-β-(n-butylthiocarbonyloxy)phenethyl]imidazole;
1-[2,4-dichloro-β-(n-pentylthiocarbonyloxy)phenethyl]imidazole;
1-[2,4-dichloro-β-(n-hexylthiocarbonyloxy)phenethyl]imidazole;
1-[2,4-dichloro-β-(p-chlorophenylthiocarbonyloxy)phenethyl]-imidazole;
1-[2,4-dichloro-β-(2,4-dichlorophenylthiocarbonyloxy)phenethyl]-imidazole;
1-[2,4-dichloro-β-(3,4-dichlorophenylthiocarbonyloxy)phenethyl]-imidazole;
1-[2,4-dichloro-β-(p-chlorobenzylthiocarbonyloxy)phenethyl]-imidazole;
1-[2,4-dichloro-β-(2,4-dichlorobenzylthiocarbonyloxy)phenethyl]-imidazole and
1-[2,4-dichloro-β-(3,4-dichlorobenzylthiocarbonyloxy)phenethyl]-imidazole.

C. Similarly, by following the procedure of part A of this example but employing a 1-[β-hydroxyphenethyl]imidazole of Formula (II) having different $R^1$ substituents and also employing different hydrocarbyl thiocarbonyl chlorides, the following compounds are prepared:

1-[4-t-butyl-β-(p-chlorobenzylthiocarboxyloxy) -imidazole; phenethyl]-imidazole;
1-[β-(2,3,4,5,6-pentachlorophenylthiocarbonyloxy)-phenethyl]-imidazole;
1-[4-chloro-β-(2,4-dichlorophenylthiocarbonyloxy)-phenethyl]-imidazole;
1-[2,4-chlorobromo-β-(ethylthiocarbonyloxy)phenethyl]imidazole; and the like.

EXAMPLE 4

Preparation of 1-[β-R-thiocarbonylthio)phenethyl]imidazoles

A. Preparation of 1-[2,4-dichloro-β-(n-butylthiocarbonyl-thio)phenethyl]imidazole The nitrate salt of 1-[2,4-dichloro-β-(ethoxythiocarbonylthio)phenethyl]imidazole (420 mg) was added under nitrogen to a stirred solution of 160 mg sodium hydroxide in 30 ml methanol at room temperature. Stirring was continued until the reaction was complete as indicated by TLC (approximately 20 minutes) and the resulting 1-[2,4-dichloro-β-(sodium thio)phenethyl]imidazole was treated with n-thiobutyryl chloride by adding the chloride directly to the solution. The mixture was stirred for 4 hours and the solvent removed by evaporation. Ether (150 ml) was added to the residue. The ether extracts were washed with water, dried (MgSO₄) and treated with nitric acid (d = 1.42) until precipitation of the nitrate salt (0.42 g) was complete. Recrystallization from ethyl acetate gave 1-[2,4-dichloro-β-(n-butylthiocarbonylthio)phenethyl]imidazole nitrate.

B. Preparation of other 1-[β-R-thiocarbonylthio)phenethyl]-imidazoles

Similarly by substituting other appropriate hydrocarbon thioncarbonyl chlorides for n-thiobutyryl chloride in Part A of this example, the following imidazoles of this invention may be prepared:

1-[2,4-dichloro-β-(n-pentylthiocarbonylthio)phenethyl]imidazole;
1-[2,4-dichloro-β-(n-hexylthiocarbonylthio)phenethyl]imidazole;
1-[2,4-dichloro-β-(n-heptylthiocarbonylthio)phenethyl]imidazole;
1-[2,4-dichloro-β-(phenylthiocarbonylthio)phenethyl]imidazole;
1-[2,4-dichloro-β-(p-fluorophenylthiocarbonylthio)-phenethyl]-imidazole;
1-[2,4-dichloro-β-(p-chlorophenylthiocarbonylthio)-phenethyl]-imidazole;
1-[2,4-dichloro-β-(benzylthiocarbonylthio)phenethyl]imidazole;
1-[2,4-dichloro-β-(p-fluorobenzylthiocarbonylthio)-phenethyl]-imidazole, and
1-[2,4-dichloro-β-(p-chlorobenzylthiocarbonylthio)-phenethyl]-imidazole.

EXAMPLE 5

Alternative Route to 1-[β-(R-carbonylthio)phenethyl]imidazoles

A. Preparation of 1-[2,4-dichloro-β-(methylcarbonylthio)-phenethyl]imidazole, oxalate.

1-(β,2,4-Trichlorophenethylimidazole (1.19G) in 5 ml of dry tetrahydrofuran was added to preformed sodium thioacetate, generated in situ from 720 mg thioacetic acid and sodium hydride (480 mg 57% dispersion in mineral oil) in 20 ml. tetrahydrofuran and the mixture stirred and refluxed under nitrogen for 18 hours. The solvent was removed under reduced pressure, water (20 ml) added and the product extracted with ether. The extracts were washed with water, dried (MgSO₄), evaporated and the residue chromatographed on silica gel eluting with 10-20% acetone in dichloromethane. The pure product in ether was treated dropwise with ethereal oxalic acid until precipitation was complete, and the thus obtained oxalate salt of 1-[2,4-dichloro-β-(methylcarbonylthio)phenethyl]imidazole recrystallized from acetone/ethyl acetate with mp By substituting other available sodium thioacids for sodium thioacetate, other compounds of this invention may be prepared.

EXAMPLE 6

Cleavage of an acid salt to a free base

The oxalate salt of 1-[2,4-dichloro-β-(2,4-dichlorophenyl-carbonyloxy)phenethyl]imidazole is prepared according the process set forth in Example 1, part A. Two (2) g of this salt suspended in 100 ml of dichloromethane is shaken with excess dilute potassium carbonate solution until the salt is completely dissolved. The organic layer is then separated, washed twice with water, and dried over magnesium sulfate. The solvent is then evaporated to yield 1-[2,4-dichloro-β-(2,4-dichlorophenylcarbonyloxy)phenethyl]imidazole in base form as an oil.

In a similar manner, the acid addition salts of all compounds of Formula (I), particularly those representatives in Examples 1-5 can be converted to the corresponding compounds in base form.

EXAMPLE 7

Acid salt formation from a free base

Nitric acid (d=1.42) is added dropwise to a stirred solution of 500 mg. of 1-[2,4-dichloro-β-(2,4-dichlorophenylcarbonyloxy)phenethyl]imidazole in 30 ml anhydrous ether until precipitation is complete. The product is filtered off, washed with ether, air dried, and recrystallized from ethyl acetate/acetone to yield 1-[2,4-dichloro-β-(2,4-dichlorophenylcarbonyloxy)phenethyl]-imidazole nitrate.

In similar manner, all compounds of Formula (I) in free base form, particularly those representatives in Examples 1-5, can be converted to the acid salts by treatment with the appropriate acid, for example, hydrochloric acid, hydrobromic acid, sulfuric acid, nitric acid, phosphoric acid, acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, or p-toluenesulfonic acid.

EXAMPLE 8

The following example is included to illustrate the preparation of representative formulations which may be used for fungi, protozoa and bacteria control.

A. Topical Formulation

| | grams |
|---|---|
| Active compound | 0.2 - 2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA(butylated hydroxy anisole) | 0.01 |
| Water      qs | 100 |

All of the above ingredients, except water, are combined and heated at 60° C. with stirring. A sufficient quantity of water at 60° C. is then added with vigorous stirring to provide 100 g. of the cream formulation which is then cooled to room temperature.

B. I.V. Formulation

| Active compound | 0.5 g. |
|---|---|
| Propylene glycol | 20 g. |
| Polyethylene glycol 400 | 20 g. |
| Tween 80 | 1 g. |
| 0.9% Saline solution qs | 100 ml. |

The active compound is dissolved in propylene glycol, polyethylene glycol 400 and Tween 80. A sufficient quantity of 0.9% saline solution is then added with stirring to provide 100 ml. of the I.V. solution which is filtered through a 0.2 micron membrane filter and packaged under sterile conditions.

C. Oral Formulation

| | parts by weight |
|---|---|
| Active compound | 200 |
| Magnesium stearate | 3 |
| Starch | 30 |
| Lactose | 116 |
| PVP (polyvinylpyrrolidone) | 3 |

The above ingredients are combined and granulated using methanol as the solvent. The formulation is then dried and formed into tablets (containing 200 mg. of active compound) with an appropriate tabletting machine.

EXAMPLE 9

A. Preparation of 1-[2,4-dichloro-β-(4-chlorobenzylthio)-phenethyl-]imidazole

To a stirred solution of 330 mg sodium hydroxide in 30 ml methanol under nitrogen is added 810 mg of 1-[2,4-dichloro-β-(methylcarbonylthio)phenethyl-]imidazole oxalate and the mixture is stirred at room temperature for ca. 30 minutes (until thin layer chromatography shows the disappearance of the ester). α,p-dichlorotoluene (350 mg) is then added, the solution stirred a further 15 minutes and the solvent removed under reduced pressure. Ether and water are then added to the residue and the ether extract washed with water, dried (MgSO₄) and concentrated. Dropwise addition of nitric acid (d = 1.42) until precipitation is complete gives the nitrate salt of 1-[2,4-dichloro-β-(4-chlorobenzylthio)phenethyl]imidazole, recrystallized from acetone, mp 130.5°–132° C.

B. By using other compounds of this invention exemplified by those set forth in Examples 2 and 4 and other suitable (substituted) hydrocarbyl halides (or mesylates, tosylates), other compounds may be prepared.

We claim as our invention:

1. A compound selected from those represented by the formula

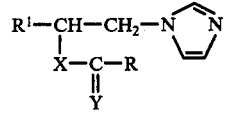   wherein

R is H, alkyl of 1 to 12 carbon atoms, phenylalkenyl of 8 to 9 carbon atoms, phenylalkyl of 7 to 9 carbon atoms, to 9 carbon atoms, phenyl, cycloalkyl of 5 to 8 ring carbon atoms, cycloalkyl lower alkyl of 6 to 9 carbon atoms, said phenylalkenyl, phenylalkyl, and phenyl each being independently optionally substituted with at least one substituent on the phenyl moiety selected from the group consisting of halo, lower alkyl, lower alkoxy, and trifluoromethyl;

$R^1$ is phenyl optionally substituted with at least one substituent selected from the group consisting of halo, lower alkyl, and trifluoromethyl; and X and Y are independently sulfur or oxygen and the antimicrobial acid addition salts thereof.

2. A compound of claim 1 wherein Y is oxygen and X is sulfur or oxygen and antimicrobial acid addition salts thereof.

3. A compound of claim 2 wherein $R^1$ is 4-halophenyl, 2,4-dihalophenyl, or 2,4,6-trichlorophenyl and the antimicrobial acid addition salts thereof.

4. A compound of claim 3 wherein R is straight chain alkyl of up to 10 carbon atoms, styryl optionally substituted on the phenyl ring with one halo at the 4-position, phenyl optionally substituted with 1 or 2 halo substituents, and benzyl optionally substituted on the phenyl ring with 1 or 2 halo substituents and the antimicrobial acid addition salts thereof.

5. A compound of claim 4 wherein $R^1$ is 2,4-dichlorophenyl and the antimicrobial acid addition salts thereof.

6. A compound of claim 5 wherein R is straight chain alkyl of 3 to 8 carbon atoms and the antimicrobial acid addition salts thereof.

7. The compound of claim 6 wherein R is n-butyl, 1-[2,4-dichloro-β-(n-butylcarbonylthio)phenethyl]imidazole and the antimicrobial acid addition salts thereof.

8. The compound of claim 6 wherein R is n-pentyl, 1-[2,4-dichloro-β-(n-pentylcarbonylthio)-phenethyl]imidazole and the antimicrobial acid addition salts thereof.

9. The compound of claim 6 wherein R is n-hexyl, 1-[2,4-dichloro-β-(n-hexylcarbonylthio)phenethyl]imidazole and the antimicrobial acid addition salts thereof.

10. The compound of claim 6 wherein R is n-heptyl, 1-[2,4-dichloro-β-(n-heptylcarbonylthio)phenethyl]imidazole and the antimicrobial acid addition salts thereof.

11. The compound of claim 6 wherein R is n-octyl, 1-[2,4-dichloro-β-(n-octylcarbonylthio)phenethyl]imidazole and the antimicrobial acid addition salts thereof.

12. A compound of claim 5 wherein R is straight chain alkyl of 3-9 carbons, phenyl substituted with chloro at 1 or 2 positions, benzyl being ring substituted with 1 or 2 chloro substituents, styryl or p-chlorostyryl and the antimicrobial acid addition salts thereof.

13. The compound of claim 12 wherein R is p-chlorophenyl, 1-[2,4-dichloro-β-(p-chlorophenylcarbonylthio)phenethyl]imidazole and the antimicrobial acid addition salts thereof.

14. The compound of claim 12 wherein R is 2,4-dichlorophenyl, 1-[2,4-dichloro-β-(2,4-dichlorophenylcarbonylthio)-phenethyl]imidazole and the antimicrobial acid addition salts thereof.

15. The compound of claim 12 wherein R is 3,4-dichlorophenyl, 1-[2,4-dichloro-β-(3,4-dichlorophenylcarbonylthio)phenethyl]imidazole and the antimicrobial acid addition salts thereof.

16. The compound of claim 5 wherein R is p-chlorobenzyl, 1-[2,4-dichloro-β-(p-chlorobenzylcarbonylthio)phenethyl]imidazole and the antimicrobial acid addition salts thereof.

17. The compound of claim 5 wherein R is 3,4-dichlorobenzyl, 1-[2,4-dichloro-β-(3,4-dichlorobenzylcarbonylthio)phenethyl]imidazole and the antimicrobial acid addition salts thereof.

18. The compound of claim 5 wherein R is 2,4-dichlorobenzyl, 1-[2,4-dichloro-β-(2,4-dichlorobenzylcarbonylthio)phenethyl]imidazole and the antimicrobial acid addition salts thereof.

19. A compound of claim 4 wherein R is straight chain alkyl of 4 to 9 carbon atoms, X and Y are O and $R^1$ is 4-chlorophenyl or 2,4-dichlorophenyl and the antimicrobial acid addition salts thereof.

20. The compound of claim 19 wherein R is n-hexyl, 1-[2,4-dichloro-β-(n-hexylcarbonyloxy)phenethyl]imidazole and the antimicrobial acid addition salts thereof.

21. The compound of claim 19 wherein R is n-heptyl, 1-[2,4-dichloro-β-(n-heptylcarbonyloxy)phenethyl]imidazole and the antimicrobial acid addition salts thereof.

22. The compound of claim 19 wherein R is n-octyl, 1-[2,4-dichloro-β-(n-octylcarbonyloxy) phenethyl]imidazole and the antimicrobial acid addition salts thereof.

23. The compound of claim 19 wherein R is n-nonyl, 1-[2,4-dichloro-β-(n-nonylcarbonyloxy)phenethyl]imidazole and the antimicrobial acid addition salts thereof.

24. A compound of claim 2 wherein R is 4-halophenyl,2,4-dihalophenyl or 3,4-dihalophenyl.

25. The compound of claim 24 wherein R is p-chlorophenyl, 1-[2,4-dichloro-β-(p-chlorophenylcarbonyloxy)phenethyl]imidazole and the antimicrobial acid addition salts thereof.

26. The compound of claim 24 wherein R is 2,4-dichlorophenyl, 1-[2,4-dichloro-β-(2,4-dichlorophenylcarbonyloxy)phenethyl]-imidazole and the antimicrobial acid addition salts thereof.

27. The compound of claim 24 wherein R is 3,4-dichlorophenyl, 1-2,4-dichloro-β-(3,4-dichlorophenylcarbonyloxy)-phenethyl]imidazole and the antimicrobial acid addition salts thereof.

28. A compound of claim 2 wherein R is 4-halobenzyl,3,4-dihalobenzyl or 2,4-dihalobenzyl.

29. The compound of claim 28 wherein R is p-chlorobenzyl, 1-[2,4-dichloro-β-(p-chlorobenzylcarbonyloxy)phenethyl]imidazole and the antimicrobial acid addition salts thereof.

30. The compound of claim 28 wherein R is 3,4-dichlorobenzyl, 1-[2,4-dichloro-β-(3,4-dichlorobenzylcarbonyloxy)-phenethyl]imidazole and the antimicrobial acid addition salts thereof.

31. The compound of claim 28 wherein R is 2,4-dichlorobenzyl, 1-[2,4-dichloro-β-(2,4-dichlorobenzylcarbonyloxy)-phenethyl]imidazole and the antimicrobial acid addition salts thereof.

32. A composition useful for inhibiting the growth of fungi, protozoa, or bacteria which comprises 0.1–10% by weight of a compound selected from those represented by the formula

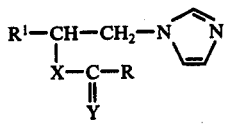

R is H, alkyl of 1 to 12 carbon atoms, phenylalkenyl of 8 to 9 carbon atoms, phenylalkyl of 7 to 9 carbon atoms, phenyl, cycloalkyl of 5 to 8 ring carbon atoms, cycloalkyl lower alkyl of 6 to 9 total carbon atoms, said phenylalkenyl, phenylalkyl, and phenyl each being independently optionally substituted with at least one substituent on the phenyl moiety selected from the group consisting of halo, lower alkyl, lower alkoxy, and trifluoromethyl;

$R^1$ is phenyl optionally substituted with at least one substituent selected from the group consisting of halo, lower alkyl, and trifluoromethyl; and X and Y are independently sulfur or oxygen and the anti-microbial acid addition salts thereof in admixture with a suitable pharmaceutically acceptable, non-toxic carrier.

33. A method of inhibiting the growth of fungi, protozoa, or bacteria which comprises applying to a host object containing or subject to attack by, fungi, protozoa, or bacteria, a fungicidally, protozoicidally, or bactericidally effective amount of a compound selected from these represented by the formula

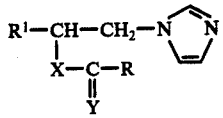 wherein

R is H, alkyl of 1 to 12 carbon atoms, phenylalkenyl of 8 to 9 carbon atoms, phenylalkyl of 7 to 9 carbon atoms, phenyl, cycloalkyl of 5 to 8 ring carbon atoms, cycloalkyl lower alkyl of 6 to 9 total carbon atoms, said phenylalkenyl, phenylalkyl, and phenyl each being independently optionally substituted with at least one substituent on the phenyl moiety selected from the group consisting of halo, lower alkyl, lower alkoxy, and trifluoromethyl;

$R^1$ is phenyl optionally substituted with at least one substituent selected from the group consisting of halo, lower alkyl, and trifluoromethyl, and X and Y are independently sulfur or oxygen and the antimicrobial acid addition salts thereof or a composition containing same as an active ingredient.

* * * * *